(12) United States Patent
Choe et al.

(10) Patent No.: US 8,195,306 B2
(45) Date of Patent: Jun. 5, 2012

(54) WIRELESS ELECTRICAL STIMULATING DEVICE FOR LIVING BODY

(75) Inventors: Ilhwan Choe, Seoul (KR); Hee Sup Shin, Gyeonggi-do (KR); Kyoobin Lee, Daejeon (KR)

(73) Assignee: Korea Institute of Science and Technology, Seoul (KR)

( * ) Notice: Subject to any disclaimer, the term of this patent is extended or adjusted under 35 U.S.C. 154(b) by 144 days.

(21) Appl. No.: 12/710,880

(22) Filed: Feb. 23, 2010

(65) Prior Publication Data

US 2010/0217350 A1    Aug. 26, 2010

(30) Foreign Application Priority Data

Feb. 23, 2009   (KR) .................. 10-2009-0014734

(51) Int. Cl.
*A61N 1/00* (2006.01)

(52) U.S. Cl. ........................................................ 607/62
(58) Field of Classification Search .................. 607/62
See application file for complete search history.

(56) References Cited

U.S. PATENT DOCUMENTS

| 7,191,010 | B2* | 3/2007 | Ohta et al. ............... 607/54 |
| 2003/0014089 | A1* | 1/2003 | Chow et al. ............... 607/54 |
| 2004/0116980 | A1* | 6/2004 | Ohta et al. ............... 607/54 |
| 2005/0187597 | A1* | 8/2005 | Vanderschuit ............ 607/88 |
| 2009/0248106 | A1* | 10/2009 | Black ....................... 607/33 |

FOREIGN PATENT DOCUMENTS

KR        1020060010145 A       2/2006

* cited by examiner

*Primary Examiner* — George Evanisko
*Assistant Examiner* — Philip Edwards
(74) *Attorney, Agent, or Firm* — Jansson Shupe & Munger Ltd.

(57) ABSTRACT

A wireless electrical stimulating device for living body comprises a light source unit for irradiating an optical signal; a light source control unit for controlling the optical signal irradiated from the light source unit; and an electrical stimulating unit for converting the optical signal received from the light source unit into an electrical signal to generate electrical stimulation. In the wireless electrical stimulating device for living body, the electrical stimulating unit comprises a battery for supplying current; an optical switch for detecting the optical signal irradiated from the light source unit to switch current supplied from the battery; and a stimulating electrode for providing the current switched by the optical switch to a living body.

6 Claims, 4 Drawing Sheets

WIRELESS ELECTRICAL STIMULATING DEVICE FOR LIVING BODY

CROSS REFERENCE TO RELATED APPLICATION

This application claims priority based on Korean patent application 10-2009-0014734, filed Feb. 23, 2009.

FIELD

Embodiments relate to an electrical stimulating device for electrically stimulating brains or nerves of living bodies, and more particularly, to a wireless electrical stimulating device for living body, which can be attached to even a small creature.

BACKGROUND

Brain stimulation technologies using electricity are used to cure patients' diseases and to disclose functions of a brain by being applied to creatures except human beings.

Electrical stimulators include wired electrical stimulators and wireless electrical stimulators. Commercialized wireless electrical stimulators are small enough not to impose a physical burden on large-sized creatures such as chimpanzees, but are not small enough to be applied to small-sized creatures such as mice.

One of implantable electrical stimulators applied to mice that are relatively small creatures weighs about 28 g (Xu et al., 2004, Journal of neuroscience methods), but cannot be applied to mice, considering that average mouse weighs about 25 g. Therefore, an electrode implanted in the head of a mouse is connected to an external large-sized electrical stimulator using a long wire so that electrical stimulation is applied to the head of the mouse through the electrode. FIG. 1 is a view illustrating an example of such a conventional electrical stimulating device for brain stimulation in mice and small animals.

In the electrical stimulating device, the mouse needs to be trained so that a wire is connected to an electrode implanted in the head of the mouse, and the wire limits the free movement of the mouse. Occasionally, the mouse severs the wire. Further, it is difficult to experiment with several mice at the same time using the wired electrical stimulating device.

Therefore, if a small-sized electrical stimulator implantable in small creatures such as mice is developed, studies using mice can be easily conducted without the aforementioned problems. If the electrical stimulator is used for studies on higher brain functions such as sociality, remarkable studies on brain functions can be made.

SUMMARY

Embodiments provide a wireless electrical stimulating device capable of ensuring the free movement of a living body to be measured and being applied to even a small living body as compared with conventional wired electrical stimulating device.

According to an exemplary embodiment, the wireless electrical stimulating device includes a light source unit for irradiating an optical signal; a light source control unit for controlling the optical signal irradiated from the light source unit; and an electrical stimulating unit for converting the optical signal received from the light source unit into an electrical signal to generate electrical stimulation.

In a preferred embodiment, the wireless electrical stimulating device includes a light source unit which provides a pulse-type optical signal and a light source control unit which controls the intensity and frequency of the electrical stimulation by controlling the amplitude and frequency of the pulse-type optical signal.

In yet another preferred embodiment, the electrical stimulating unit includes a battery for supplying current, an optical switch for detecting the optical signal irradiated from the light source unit to switch current supplied from the battery, and a stimulating electrode for providing the current switched by the optical switch to a living body. In another preferred embodiment, the optical switch is a phototransistor of which electrical resistance is changed in inverse proportion to the intensity of the optical signal irradiated from the light source unit and the optical signal is an infrared signal. In another preferred embodiment, the light source unit comprises a plurality of infrared light emitting diodes (LEDs) and controls the amount of light by adjusting the number of the infrared LEDs and the arrangement angle between the infrared LEDs.

In yet another preferred embodiment, the light source unit comprises an LED line having a plurality of infrared LEDs. In another preferred embodiment, the plurality of infrared LEDs are spaced apart from each other at regular intervals, the LED line comprises a plurality of LED lines and the plurality of LED lines are parallel with each other. In addition, the plurality of LED lines include first and second LED lines which are adjacent to each other, and a first infrared LED in the first LED line and a second infrared LED in the second LED line are disposed such that the angle made by the straight line obtained by connecting the centers of the first and second infrared LEDs and the straight line formed by connecting the centers of the plurality of infrared LEDs in the second LED line becomes 60 degrees. In addition, the first infrared LED in the first LED line and the second infrared LED in the second LED line are the closest to a vertical line drawn from the first infrared LED to a straight line formed by connecting the centers of a plurality of infrared LEDs in the second LED line.

BRIEF DESCRIPTION OF THE DRAWINGS

In order that the advantages of the invention will be readily understood, a more detailed description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Figure 1:
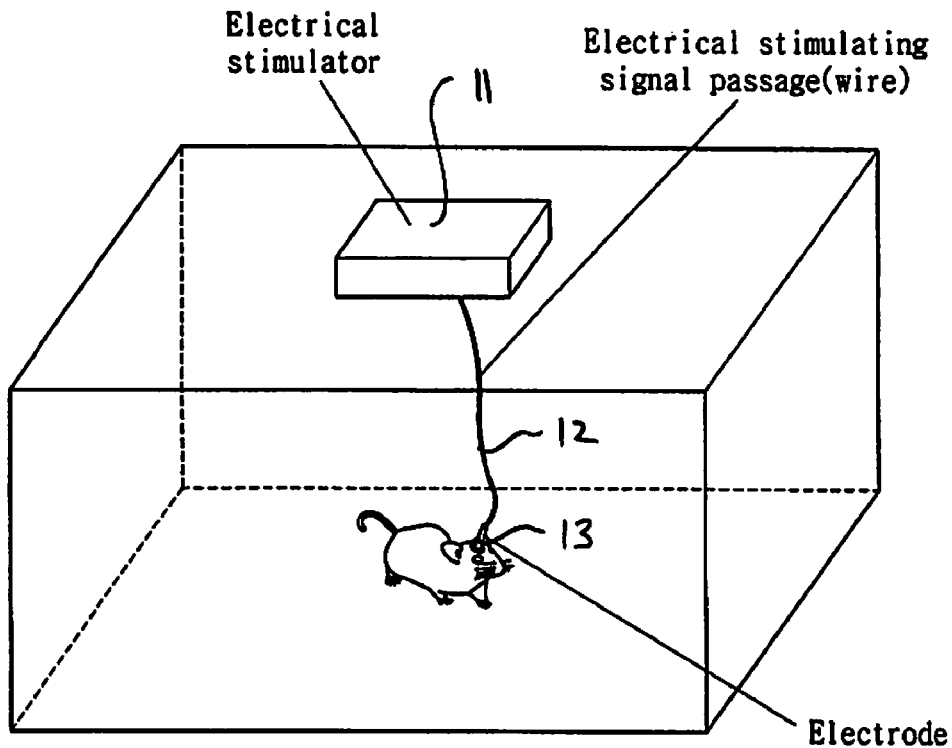
FIG. 1 illustrates an example of a conventional electrical stimulating device for brain.

Exemplary embodiments will now be described more fully hereinafter with reference to the accompanying drawings, in which exemplary embodiments are shown. This disclosure may, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item. The use of the terms "first", "second", and the like does not imply any particular order, but they are included to identify individual elements. Moreover, the use of the terms first, second, etc. does not denote any order or importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In the drawings, like reference numerals in the drawings denote like elements. The shape, size and regions, and the like, of the drawing may be exaggerated for clarity.

Many of the functional units described in this specification have been labeled as modules, in order to more particularly emphasize their implementation independence. For example, a module may be implemented as a hardware circuit comprising custom circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically, comprise the module and achieve the stated purpose for the module.

A module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

Reference throughout this specification to "exemplary embodiment," "one embodiment," "an embodiment," or similar language means that a particular feature, structure, or characteristic described in connection with the embodiment is included in at least one embodiment of the present invention. Thus, appearances of the phrases "exemplary embodiment," "in one embodiment," "in an embodiment," and similar language throughout this specification may, but do not necessarily, all refer to the same embodiment.

Figure 2:
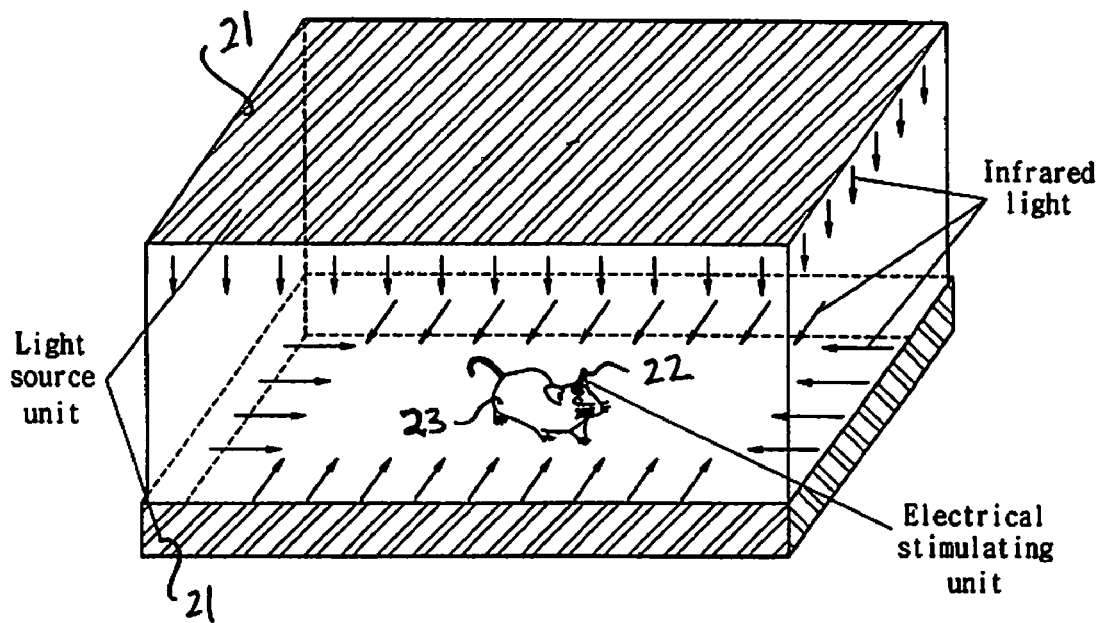
FIG. 2 is a perspective view of a wireless electrical stimulating device according to an exemplary embodiment.

FIG. 2 is a view illustrating a wireless electrical stimulating device for living body according to an exemplary embodiment. The wireless electrical stimulating device according to the exemplary embodiment comprises a light source unit 21 and an electrical stimulating unit 22 for applying an electrical stimulation to a living body. The wireless electrical stimulating device may further comprise a light source control unit (not shown).

In FIG. 2, the hexahedron shows outer walls of the wireless electrical stimulating device. The light source unit 21 is disposed at the top and lower portion of the hexahedron. The diagonally lined portion indicates the light source unit. The electrical stimulating unit 22 is attached to the head of a mouse that is an experimental subject. The light source unit 21 controlled by the light source control unit irradiates an optical signal, and the electrical stimulating unit applies an electrical stimulation signal to a living body (e.g., the mouse) in response to the optical signal.

In conventional electrical stimulating devices, an electrical signal is generated from an electrical signal generator or electrical stimulator 11, and the generated electrical signal is applied to a living body through a wire 12 and an electrode 13 as shown in FIG. 1. In the wireless electrical stimulating device of the exemplary embodiment of FIG. 2, an optical signal is irradiated using the light source unit 21, and the electrical stimulating unit 22 converts the optical signal into an electrical stimulation signal, thereby applying the electrical stimulation signal to a living body. The wireless electrical stimulating device is used to ensure the free movement of the living body without using the connected wire required by the conventional electrical stimulating device of FIG. 1.

The electrical stimulating unit is attached to the brain or nerves of a small creature (the head of a mouse 23 as illustrated in FIG. 2). In the electrical stimulating unit 22, a micro battery may be used as a power source, and a phototransistor may be used as an optical switch. Optical signals for operating electrical stimulating unit 22 are irradiated to the electrical stimulating unit. In the exemplary embodiment of FIG. 2, infrared light (100 Hz and 100 μs) can be irradiated to apply high frequency electrical stimulation to the brain or nerves of the mouse, thereby inducing a curative effect, a behavioral change, an electro-physiological change or the like.

Electrical stimulating unit 22 is a unit having a maximally reduced burden imposed in a living body implant by decreasing the size and weight thereof. The electrical stimulating unit may be manufactured to have a weight of about 0.65 to about 0.7 g and a volume of about 200 to about 290 $mm^3$. An operating power source may be used at a continuous current of about 4 μA (load: about 300 kΩ and about 9 to about 10V) for about 200 hours or more. If the operating power source is controlled by a switching unit through light, high frequency electrical stimulation can be applied to a living body, and therefore, neurons of the living body can be activated, thereby inducing a curative effect or a behavioral change. Meanwhile, the aforementioned numerical values are merely illustrative of an exemplary embodiment and do not limit the scope of the invention.

When electrical stimulation is applied to a brain, it is important to activate neurons in the brain. In the brain, pulse-type current usually activates neurons rather than direct current, and important variables are intensity, duration and frequency of the pulse. For the frequency of the pulse, the electrical stimulation is divided into low frequency stimulation (LFS) having a frequency of about 10 Hz and high frequency stimulation (HFS) having a frequency of about 100 Hz. However, the physiological effects of both stimulations have not been apparently clarified. HFS having about 3 to about 4V, about 60 to about 40 μs and about 100 Hz is applied to Parkinson's disease patients for the purpose of symptom reduction.

Rheobase current is the minimum amount of electricity that will produce a stimulated response, and, specifically the minimum amount of current for activating neurons. Rheobase can be further defined as the minimal electrical amplitude of infinite duration (practically, a few hundred milliseconds) that results in an action potential or the contraction of a muscle. Specifically, in the case of a nerve or single muscle cell, rheobase is half the current that needs to be applied for the duration of chronaxie to result in an action potential, muscle twitch or neuron activation. Chronaxie current is two (2) times larger than the rheobase current and is defined as the minimum time over which an electric current double the strength of the rheobase current needs to be applied, in order to stimulate a muscle fiber, nerve cell, neuron activation or the like. When calculating the threshold current of activating neurons based on the duration of pulses, the threshold current is increased as the duration is shortened and rapidly increased as it exceeds the chronaxie current.

Myelinated axons are activated at a pulse duration of about 30 to about 200 μs, and cell bodies and dendrites are activated at a pulse duration of about 1 to about 10 ms. If a short pulse having a low voltage is applied to neurons, target neural elements are activated in a narrow area. If a short pulse having a high voltage is applied to the neurons, the target neural elements are activated in a broad area. Thus, the target neural elements and non-target neural elements are activated together. If a long pulse having a low voltage is applied to the neurons, a large number of target neural elements are activated in a narrow area.

The photoelectric effect is used in converting light into current, and semiconductor elements such as a photodiode, a phototransistor and a solar cell are developed using the technology. The technology is widely used to manufacture solar cells, cameras and the like. In addition, it is possible to manufacture a semiconductor that operates based on a specific waveform with a specific range of light. Among these elements, the phototransistor may be used to form switches due to the property that if light is incident onto the phototransistor, its resistance is decreased. An element that reacts to a specific infrared light (about 700 to about 1100 ns) may be formed by providing a filter on the phototransistor, and may be operated as an on/off switch at light of about 100 lux.

Phototransistors are similar in operation to the amplifying transistors, but they are controlled by light rather than by the electric current of an emitter. Phototransistors typically use a germanium disk and only a single collector wire connected to the germanium disk which is typically very thin, on the order of three thousandths of an inch thick. Light focused on one side of the disk controls the flow of current in the wire, thus making a control device similar in function to a photo-electric cell. Phototransistors have relatively high power output and provide quality response to a rapidly fluctuating light source. Phototransistors are sensitive to the wavelengths of light given off by ordinary incandescent light bulbs, LEDs and the like and are well suited to operate with these easily available sources with good fidelity. Another virtue is the device's low impedance.

A light emitting diode (LED), a laser or the like is used as the light source for irradiating light onto a semiconductor. The LED is operated at low voltage and low current, and its optical property does not harm living bodies. Since the LEDs have fast operating speeds, LEDs may be operated at high frequency pulses of a few tens of kHz. Since one type of commercialized infrared LEDs has a rise time of about 2 μs and a radiant flux of about 15 mW, the infrared LED can activate an infrared phototransistor positioned at a distance of over 40 cm therefrom.

Figure 3A:
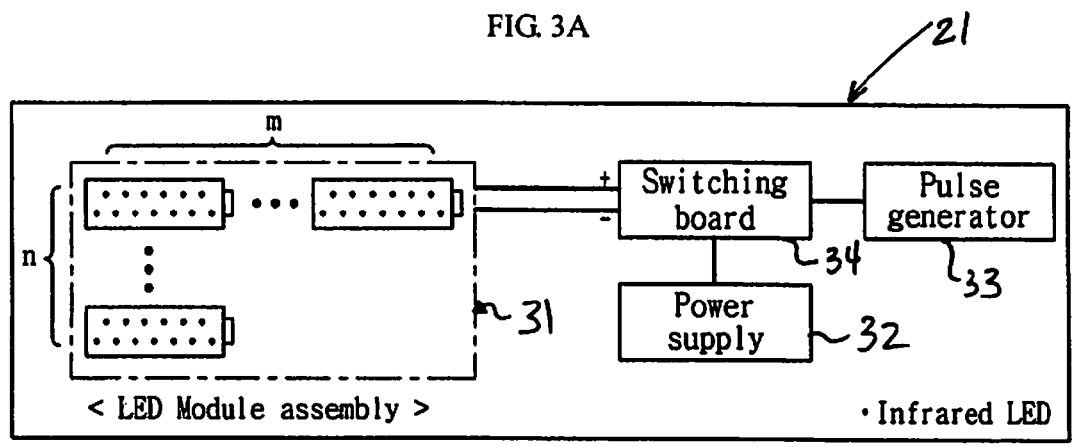
FIGS. 3A to 3C are views illustrating light source units according to exemplary embodiments.
Figure 3B:
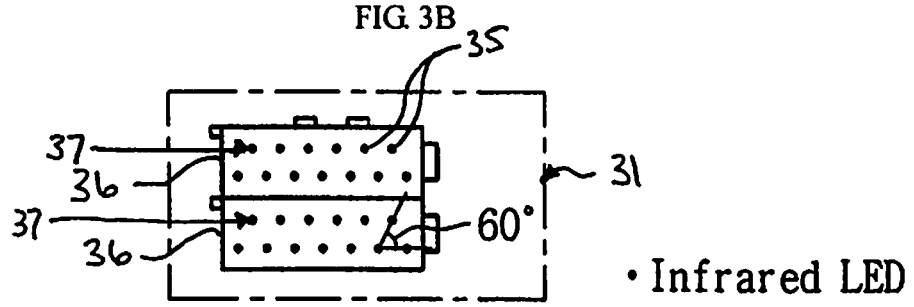
Figure 3C:
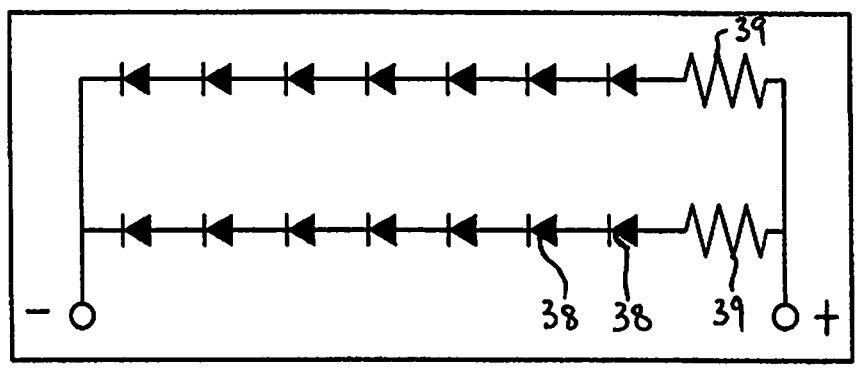

FIGS. 3A, 3B and 3C are views illustrating a light source unit according to an exemplary embodiment. The light source unit irradiates optical signals to operate the electrical simulating unit. In the exemplary embodiment of FIG. 2, the light source unit 21 irradiates infrared light, and therefore, an infrared LED is used as the light source unit. FIG. 3A is a view illustrating the entire configuration of the light source unit 21. The light source unit may be manufactured to produce a light field with a desired area by assembling light emitting module assemblies 31. The light source unit 21 is connected to a power supply 32 and operated by energy supplied by the power supply. The light source unit 21 is turned on/off under the control of a pulse generator 33 and a switching board 34.

FIG. 3B is a view illustrating an example of one configuration of LED module assembly 31 used as the light source unit. A plurality of LEDs 35 are included in LED module 31. The plurality of LEDs are manufactured as a module 36, thereby controlling the intensity of light field. The LED module 35 comprises an LED line 36 having LEDs disposed at regular intervals. The LED module 35 may comprise a plurality of LED lines 37. The plurality of LED lines are typically disposed parallel to each other.

The arrangement of the plurality of LED lines 37 may be described using the arrangement of two LED lines 37 adjacent to each other. When assuming that the two LED lines adjacent to each other are first and second LED lines, respectively, an infrared LED included in the first LED line is referred to as a first infrared LED, and an infrared LED closest to a vertical line drawn from the first infrared LED to a straight line connecting the infrared LEDs of the second LED line (hereinafter, referred to as a 'straight line of the second LED line') is referred to as a second infrared LED. The LED lines may be arranged so that the angle made by the straight line obtained by connecting the centers of the first and second infrared LEDs and the straight line of the second LED line becomes about 60 degrees. As such, the LED lines are arranged, so that the light source unit can effectively irradiate optical signals and so that the dead zone of light can be reduced.

FIG. 3C is a circuit diagram of LED module 31. LED module 31 is typically constructed of a plurality of light emitting diodes 38 in series with a resistor 39.

Figure 4A:
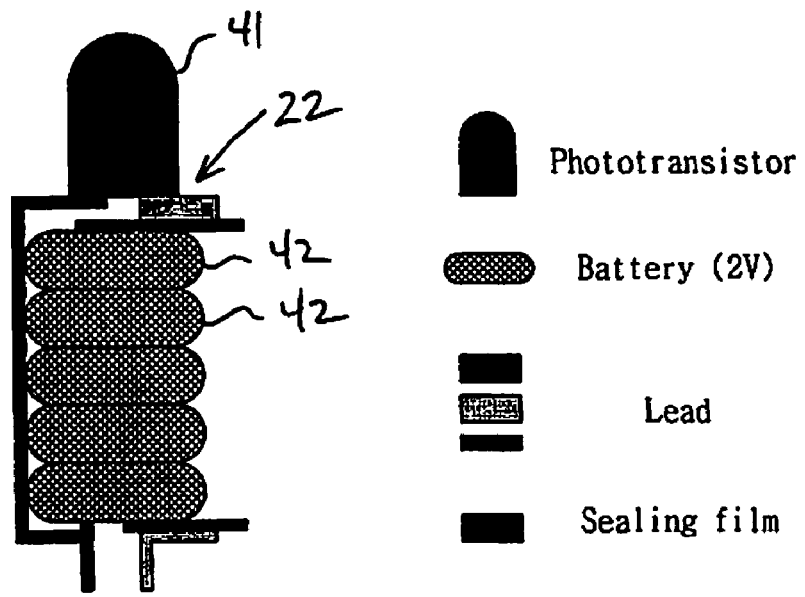
FIGS. 4A and 4B are views illustrating exemplary embodiments of electrical stimulating units.
Figure 4B:
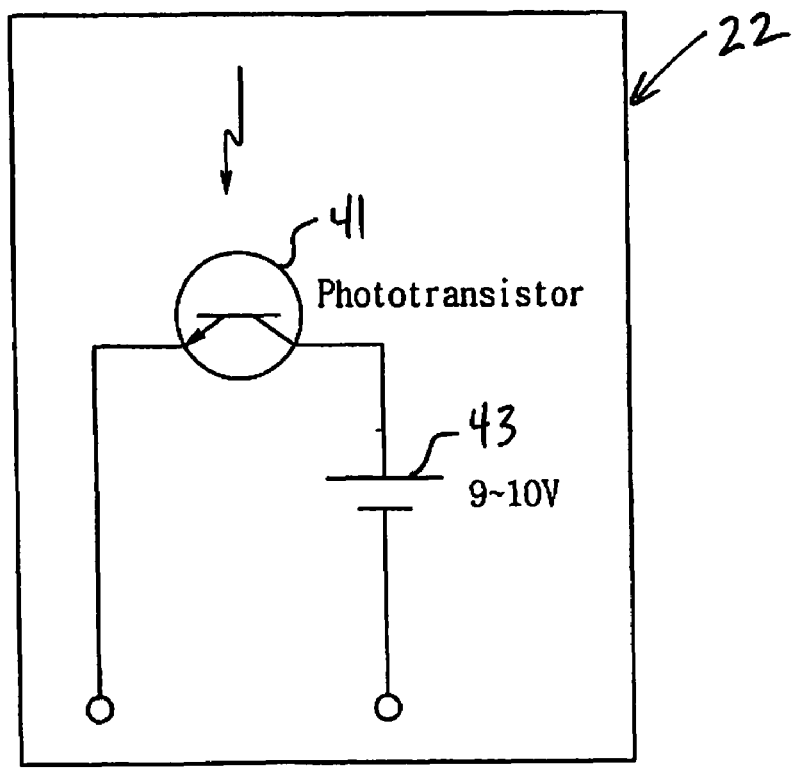

FIGS. 4A and 4B are views illustrating an electrical stimulating unit 22. FIG. 4A is a view of an element constituting the electrical stimulating unit 22, and FIG. 4B is a circuit diagram of electrical stimulating unit 22. As can be seen, electrical stimulating unit 22 includes a phototransistor 41 coupled with several 2V batteries 42. In a preferred embodiment, five (5) batteries 42 are placed is series for a total of 9-10V (43) as shown.

Figure 5:
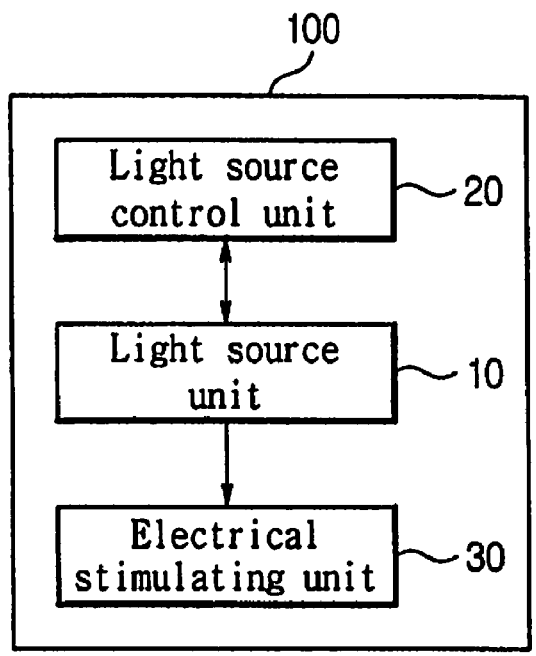
FIG. 5 is a block diagram of the wireless electrical stimulating device according to an exemplary embodiment.

FIG. 5 is a block diagram of the wireless electrical stimulating device according to yet another exemplary embodiment. The wireless electrical stimulating device 100 for living body according to the exemplary embodiment comprises a light source unit 10 for irradiating optical signals; a light source control unit 20 for controlling the optical signals received from the light source unit 10; and an electrical stimulating unit 30 for converting the optical signals irradiated from the light source unit 10 into electrical signals to generate electrical stimulations.

The light source unit 10 irradiates a pulse-type optical signal. The electrical stimulating unit 30 applies a pulse-type voltage to a brain or nerves in response to the input of the optical signal. Conditions of the inputted signal may be controlled by the light source control unit 20, and current may be applied to satisfy conditions of voltage and current at which neurons of an actual living body are activated. Thus, as shown in FIG. 2, mouse 23 may move while receiving pulse electrical simulation applied from the light source unit 10, 21 in a previously defined light field range.

The electrical stimulating unit 30 is connected to the brain or nerves of mouse 23 through an electrode for applying a voltage to the brain or nerves of mouse 23. A micro battery such as battery 31 in FIG. 6 may be included in electrical stimulating unit 30. If a phototransistor receives an optical signal irradiated from the light source unit 10, the resistance of the phototransistor is decreased, and therefore, current flows in the electrical stimulating unit 30. The phototransistor is generally used as an on/off switch by controlling the distance between the light source unit 10 and phototransistor 41. Further, the amplitude and frequency of the current flowing in the electrical stimulating unit 30 may be controlled based on the intensity and frequency of the optical signal.

The light source unit 21, 10 and the light source control unit 20 are positioned at the top and lower portion of the hexahedron in the wireless electrical stimulating device of the exemplary embodiment, and electrical stimulating unit 22, 30 is attached to a living body (e.g., a mouse). Thus, an experiment or test can be performed without preventing the movement of the living body.

Figure 6:
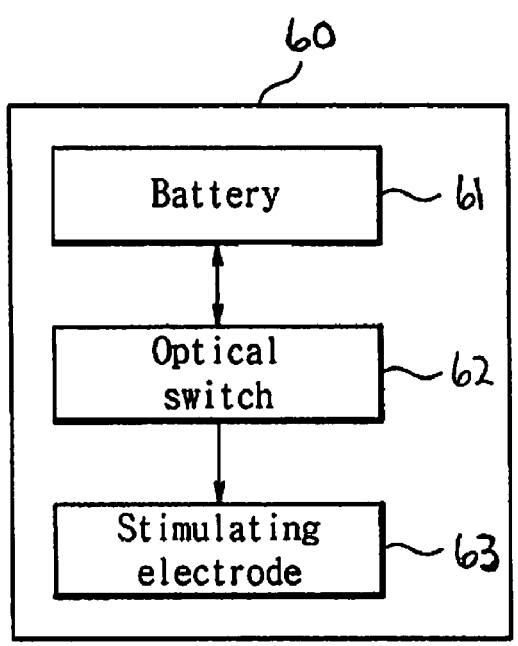
FIG. 6 is a block diagram of the electrical stimulating unit according to an exemplary embodiment.

FIG. 6 is a block diagram of the electrical stimulating unit 60 according to an exemplary embodiment. The electrical stimulating unit 60 according to the exemplary embodiment may comprise a battery 61 for supplying current; an optical switch 62 for detecting optical signals of the light source unit 10 to switch current supplied from the battery 61; and a stimulating electrode 63 for applying the current switched by the optical switch 62 to a living body.

Wireless electrical stimulating device 22, 30 is miniaturized, the voltage and current delivery requirements of battery 61 is necessarily reduced. The optical switch 62 reacts to the optical signal producing a stimulating current. Stimulating current flows in a circuit by detecting an optical signal and performing switching based on the intensity or frequency of the optical signal. The stimulating electrode 63 is implanted in a living body so as to supply current switched by the optical switch 62 to the living body for stimulating the brain, selected neurons and the like. If infrared light is used as the optical signal, an optical switch which reacts to the infrared light will be used. Therefore, such an operation can be performed by proving a filter associated with the optical switch. The filter selectively transmits light with a specific waveform range as required by the specific application.

In conventional stimulators, electrical stimulation signals are applied to a living body through a wire from the electrical stimulator to the electrode implanted in the living body. However, in the wireless electrical stimulating device according to an exemplary embodiment, the optical signals are converted into electrical stimulation signals, thereby eliminating the need for a wired connection. Accordingly, the small size and lightweight of the wireless electrical stimulating device can be achieved.

Further, the experiment for applying neural stimulation to several mice without external interference while not interrupting the movement of the mice can be performed using the wireless electrical stimulating device.

While specific component values have been show for ease of illustration and description, it should be understood that a variety of combination of values is possible and contemplated by the present invention. Further, while specific connections have been used and shown for ease of description, it should also be understood that a variety of connection points are possible and may vary depending on the specifics of the application and circuit used.

While the present invention has been described in connection with certain exemplary or specific embodiments, it is to be understood that the invention is not limited to the disclosed embodiments, but, on the contrary, is intended to cover various modifications, alternatives, modifications and equivalent arrangements as will be apparent to those skilled in the art. Any such changes, modifications, alternatives, modifications, equivalents and the like may be made without departing from the spirit and scope of the invention.

What is claimed is:

1. A wireless electrical stimulating device for living body, comprising:
   a light source unit for irradiating an optical signal;
   a light source control unit for controlling the optical signal irradiated from the light source unit; and
   an electrical stimulating unit for converting the optical signal received from the light source unit into an electrical signal to generate electrical stimulation, wherein:
   the light source unit comprises a plurality of LED lines parallel with each other;
   each of the plurality of LED lines has a plurality of infrared LEDs spaced apart from each other at regular intervals;
   first and second LED lines among the plurality of LED lines are adjacent to each other; and
   a first infrared LED in the first LED line and a second infrared LED in the second LED line, which is closest to a vertical line drawn from the first infrared LED to a straight line formed by connecting the centers of a plurality of infrared LEDs in the second LED line, are disposed such that the angle made by the straight line obtained by connecting the centers of the first and second infrared LEDs and the straight line formed by connecting the centers of the plurality of infrared LEDs in the second LED line is 60 degrees.

2. The wireless electrical stimulating device of claim 1 wherein the light source unit provides a pulse-type optical signal.

3. The wireless electrical stimulating device of claim 2 wherein the light source control unit controls the intensity and frequency of the electrical stimulation by controlling the amplitude and frequency of the pulse-type optical signal.

4. The wireless electrical stimulating device of claim 1 wherein the electrical stimulating unit comprises:
   a battery for supplying current;
   an optical switch for detecting the optical signal irradiated from the light source unit to switch current supplied from the battery; and
   a stimulating electrode for providing the current switched by the optical switch to a living body.

5. The wireless electrical stimulating device of claim 4 wherein the optical switch is a phototransistor of which electrical resistance is changed in inverse proportion to the intensity of the optical signal irradiated from the light source unit.

6. The wireless electrical stimulating device of claim 5 wherein the optical signal is an infrared signal.

* * * * *